United States Patent [19]
Inouye et al.

[11] Patent Number: 4,647,572
[45] Date of Patent: * Mar. 3, 1987

[54] IODOALLYL AND IODOPROPARGYL SUBSTITUTED TETRAZOLES AND ANTI-MICROBIAL COMPOSITIONS THEREOF

[75] Inventors: Shigeharu Inouye; Masao Koyama; Keinosuke Miyauchi, all of Yokohama; Takashi Tsuruoka, Kawasaki; Fumio Kai, Fujisawa; Kuniomi Matsumoto, Machida; Taro Niida; Eiichi Akita, both of Yokohama, all of Japan

[73] Assignee: Meiji Seika Kaisha, Ltd., Tokyo, Japan

[*] Notice: The portion of the term of this patent subsequent to Jan. 7, 2003 has been disclaimed.

[21] Appl. No.: 545,061

[22] Filed: Oct. 25, 1983

[30] Foreign Application Priority Data

Oct. 29, 1982 [JP] Japan ................. 57-191569

[51] Int. Cl.[4] ................. A61K 31/41; C07D 257/04
[52] U.S. Cl. ................. 514/381; 548/250; 548/252; 548/253
[58] Field of Search ................. 548/250, 252, 253; 424/269; 514/381

[56] References Cited
U.S. PATENT DOCUMENTS
4,563,472  1/1986  Inouye et al. ................. 548/250

FOREIGN PATENT DOCUMENTS
47-39099  10/1972  Japan .
57-1472   6/1982   Japan .
58-183672 6/1982   Japan .

OTHER PUBLICATIONS
Finnegan et al., J.A.C.S., 80, 1958 pp. 3908–3911.

Primary Examiner—Richard L. Raymond
Assistant Examiner—David B. Springer
Attorney, Agent, or Firm—James J. Ralabate

[57] ABSTRACT

Triiodoallyl- or iodopropargyl-substituted tetrazole compounds which are prepared by reacting substituted tetrazole compound with reactive derivatives of corresponding triiodoallyl alcohol or iodopropargyl alcohol or by iodinating propargyltetrazole compounds, as well as antibacterial and antifungal compositions for medicinal, agricultural and industrial fields which contain as active ingredient said tetrazole compounds.

4 Claims, No Drawings

IODOALLYL AND IODOPROPARGYL SUBSTITUTED TETRAZOLES AND ANTI-MICROBIAL COMPOSITIONS THEREOF

PRIOR ART

It has been hitherto known in the art that 2,3,3-triiodoallyl alcohol, alkyl ethers thereof and aralkyl ethers thereof can show antibacterial and antifungal activities (See, Japanese Patent Publications No. 20484/1978, No. 20006/1978 and No. 39099/1972). However, many of these compounds do not always show satisfactory antibacterial and antifungal activities and, particularly, they have disadvantages such as inferior ex vitro therapeutic ratio in animal experiments against diseases cuased by, for example, bacteria and fungi.

The present inventors previously found out that triiodopropargyl- or iodoallyl-pyrrole compounds exert antibacterial and antifungal activities and disclosed and claimed said compounds, their preparation and their antibacterial and antifungal uses in their co-pending Japanese patent applications No. 6609/1982 and No. 160557/1981. Further, the present inventors found out that iodopropargyl- or triiodoallyl-triazole, tetrazole, 5-acetylaminotetrazole, 5-methyltetrazole or triiodoallyl-5-phenyltetrazole compounds exert antibacterial and antifungal activities and disclosed and claimed said compounds, their preparation and antibacterial and antifungal uses in their co-pending Japanese patent applications No. 64759/1982 and No. 112404/1982.

OBJECT OF THE INVENTION

An object of this invention is to provide 2,3,3-triiodoallyl- and iodopropargyl-substituted tetrazole compounds, which are new substances exhibiting inhibitory activity against a wide variety of fungi, gram-positive and gram-negative bacteria with low toxicity and less irritant property, processes for preparing the same as well as antibacterial and antifungal compositions for medicinal, agricultural and industrial uses containing as an active ingredient said compounds.

DETIALED DESCRIPTION OF THE INVENTION

This invention relates to a tetrazole compound having the formula (I)

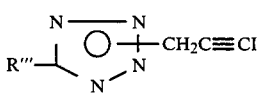
(I)

wherein
X is a group of —C≡CI or a group of

when X is a group of —C≡CI, R is an alkyl group, a phenyl group, a substituted phenyl group (wherein a 3-chloro-2-nitrophenyl group is excluded) or a benzyl group; and,
when X is a group of

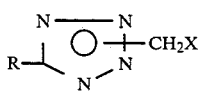

R is an alkyl group having two or more carbon atoms, a substituted phenyl group (wherein a 3-chloro-2-nitrophenyl group is excluded) or a benzyl group;
a process for preparing a tetrazole compound having the fomrula (I-a)

(I-a)

wherein
R' is an alkyl group having two or more carbon atoms, a substituted phenyl group (wherein a 3-chloro-2-nitrophenyl group is excluded) or a benzyl group
which comprises reacting a tetrazole derivative of the formula (II)

(II)

wherein
R' is as defined above with an iodide compound of the formula (III)

$$Y—CH_2X \qquad (III)$$

wherein
X is as defined above, and
Y is a halogen atom or a group of R"—SO$_2$—O— (wherein R" is an alkyl group, an aryl group or a substituted aryl group),
a process for preparing an iodopropargyltetrazole compound having the fomrula (I-b)

(I-b)

wherein
R'" is an alkyl group, a phenyl group, a substituted phenyl group (wherein a 3-chloro-2-nitrophenyl group is excluded) or a benzyl group
which comprises iodination of a propargyltetrazole compound of the formula (IV)

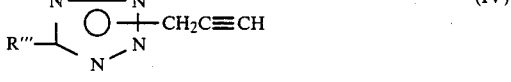
(IV)

wherein
R'" is as defined above;
as well as an antibacterial and antifungal composition which comprises as an active ingredient the tetrazole compound having the above formula (I).

In the present compound having the formula (I), the tetrazole-substituent R may be exemplified, for instance, by an alkyl group such as methyl, ethyl, propyl, isopropyl, butyl, isobutyl, sec.-butyl, tert.-butyl, pentyl, hexyl, heptyl, decyl and the like; a phenyl group; a substituted phenyl group such as methoxyphenyl, chlorophenyl, fluorophenyl, dichlorophenyl, methylphenyl, trifluoromethylphenyl, cyanophenyl, hydroxyphenyl, carbamoylphenyl, nitrophenyl, carboxyphenyl, dimethylaminophenyl and the like; and a benzyl group.

The present compounds having the formula (I) are all novel compounds and, as representative examples thereof, there may be recited the following compounds.

| Compound No. | Compound |
| --- | --- |
| 1 | 2-(1'-iodopropyn-3'-yl-5-methyltetrazole |
| 2 | 1-(1'-iodopropyn-3'-yl-5-methyltetrazole |
| 3 | 2-(1'-iodopropyn-3'-yl)-5-ethyltetrazole |
| 4 | 1-(1'-iodopropyn-3'-yl)-5-ethyltetrazole |
| 5 | 2-(1'-iodopropyn-3'-yl)-5-n-propyltetrazole |
| 6 | 1-(1'-iodopropyn-3'-yl)-5-n-propyltetrazole |
| 7 | 2-(1'-iodopropyn-3'-yl)-5-isopropyltetrazole |
| 8 | 1-(1'-iodopropyn-3'-yl)-5-isopropyltetrazole |
| 9 | 2-(1'-iodopropyn-3'-yl)-5-butyltetrazole |
| 10 | 1-(1'-iodopropyn-3'-yl)-5-butyltetrazole |
| 11 | 2-(1'-iodopropyn-3'-yl)-5-decyltetrazole |
| 12 | 1-(1'-iodopropyn-3'-yl)-5-decyltetrazole |
| 13 | 2-(1'-iodopropyn-3'-yl)-5-isobutyltetrazole |
| 14 | 1-(1'-iodopropyn-3'-yl)-5-isobutyltetrazole |
| 15 | 2-(1'-iodopropyn-3'-yl)-5-tert.-butyltetrazole |
| 16 | 1-(1'-iodopropyn-3'-yl)-5-tert.-butyltetrazole |
| 17 | 2-(1'-iodopropyn-3'-yl)-5-pentyltetrazole |
| 18 | 1-(1'-iodopropyn-3'-yl)-5-pentyltetrazole |
| 19 | 2-(1'-iodopropyn-3'-yl)-5-hexyltetrazole |
| 20 | 1-(1'-iodopropyn-3'-yl)-5-hexyltetrazole |
| 21 | 2-(1'-iodopropyn-3'-yl)-5-heptyltetrazole |
| 22 | 1-(1'-iodopropyn-3'-yl)-5-heptyltetrazole |
| 23 | 2-(2'-iodopropyn-3'-yl)-5-phenyltetrazole |
| 24 | 2-(1'-iodopropyn-3'-yl)-5-(p-methoxyphenyl)-tetrazole |
| 25 | 2-(1'-iodopropyn-3'-yl)-5-(p-chlorophenyl)-tetrazole |
| 26 | 1-(1'-iodopropyn-3'-yl)-5-(p-chlorophenyl)-tetrazole |
| 27 | 2-(1'-iodopropyn-3'-yl)-5-(o-chlorophenyl)-tetrazole |
| 28 | 2-(1'-iodopropyn-3'-yl)-5-(m-chlorophenyl)-tetrazole |
| 29 | 2-(1'-iodopropyn-3'-yl)-5-(p-fluorophenyl)-tetrazole |
| 30 | 2-(1'-iodopropyn-3'-yl)-5-(3'',5''dichlorophenyl)-tetrazole |
| 31 | 2-(1'-iodopropyn-3'-yl)-5-(p-methylphenyl)-tetrazole |
| 32 | 2-(1'-iodopropyn-3'-yl)-5-(m-trifluoromethylphenyl)tetrazole |
| 33 | 2-(1'-iodopropyn-3'-yl)-5-(p-cyanophenyl)-tetrazole |
| 34 | 2-(1'-iodopropyn-3'-yl)-5-(p-hydroxyphenyl)-tetrazole |
| 35 | 1-(1'-iodopropyn-3'-yl)-5-(p-hydroxyphenyl)-tetrazole |
| 36 | 2-(1'-iodopropyn-3'-yl)-5-(p-carbamoylphenyl)-tetrazole |
| 37 | 2-(1'-iodopropyn-3'-yl)-5-(p-nitrophenyl)tetrazole |
| 38 | 2-(1'-iodopropyn-3'-yl)-5-(p-carboxyphenyl)-tetrazole |
| 39 | 2-(1'-iodopropyn-3'-yl)-5-(p-dimethylaminophenyl)tetrazole |
| 40 | 2-(2',3',3'-triiodoallyl)-5-n-heptyltetrazole |
| 41 | 1-(2',3',3'-triiodoallyl)-5-n-heptyltetrazole |
| 42 | 2-(2',3',3'-triiodoallyl)-5-n-pentyltetrazole |
| 43 | 1-(2',3',3'-triiodoallyl)-5-n-pentyltetrazole |
| 44 | 2-(2',3',3'-triiodoallyl)-5-tert.-butyltetrazole |
| 45 | 1-(2',3',3'-triiodoallyl)-5-tert.-butyltetrazole |
| 46 | 2-(2',3',3'-triiodoallyl)-5-n-propyltetrazole |
| 47 | 1-(2',3',3'-triiodoallyl)-5-n-propyltetrazole |
| 48 | 2-(2',3',3'-triiodoallyl)-5-isopropyltetrazole |
| 49 | 1-(2',3',3'-triiodoallyl)-5-isopropyltetrazole |
| 50 | 2-(2',3',3'-triiodoallyl)-5-ethyltetrazole |
| 51 | 1-(2',3',3'-triiodoallyl)-5-ethyltetrazole |
| 52 | 2-(2',3',3'-triiodoallyl)-5-n-butyltetrazole |
| 53 | 1-(2',3',3'-triiodoallyl)-5-n-butyltetrazole |
| 54 | 2-(2',3',3'-triiodoallyl)-5-isobutyltetrazole |
| 55 | 1-(2',3',3'-triiodoallyl)-5-isobutyltetrazole |
| 56 | 2-(2',3',3'-triiodoallyl)-5-decyltetrazole |
| 57 | 1-(2',3',3'-triiodoallyl)-5-decyltetrazole |
| 58 | 2-(2',3',3'-triiodoallyl)-5-benzyltetrazole |
| 59 | 1-(2',3',3'-triiodoallyl)-5-benzyltetrazole |

The compound of the formula (I) according to this invention may be prepared according to the following reaction schema A:

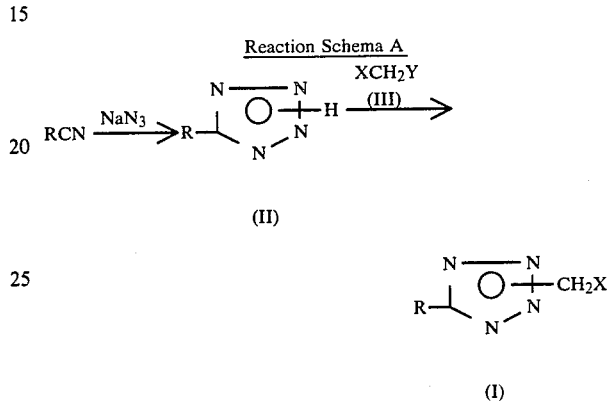

In the above formulae, R, X and Y are as defined above. The 5-substituted tetrazole (II), which may be employed in this reaction schema, may be easily prepared according to the conventional reaction of nitrile with an azide compound, for instance, by the procedures as disclosed in, e.g. "Synthesis", page 71, 1973 or by modification thereof.

As shown above, the 5-substituted tetrazole (II) is reacted with a reactive derivative of iodopropargyl alcohol or 2,3,3-triiodoallyl alcohol (III) to produce the end product of this invention, namely the triiodoallyl-sustituted tetrazole or iodopropargyl-substituted tetrazole compound (I).

The 3-iodopropargyl alcohol or 2,3,3-triiodoallyl alcohol reactive derivative (III) may be prepared by reacting the corresponding alcohol with a halogenating agent such as thionyl chloride or thionyl bromide or with an arylsulfonic acid derivative such as methanesulfonic acid anhydride, benzenesulfonyl chloride, p-toluenesulfonyl chloride, p-nitrobenzenesulfonyl chloride. In particular, where the 3-iodopropargyl alcohol or 2,3,3-triiodoallyl alcohol esterified with an arylsulfonic acid derivative having an electron attractive substituent is employed, the reaction may be proceed rapidly and even the reaction with a lower reactive tetrazole compound may also proceed easily.

The reaction of the above 5-substituted tetrazole (II) with the above iodopropargyl alcohol or 2,3,3-triiodoallyl alcohol reactive derivative (III) is the N-alkylation reaction wherein the 5-substituted tetrazole (II) is dissolved or suspended in an inert organic solvent and a base and the iodopropargyl alcohol or 2,3,3-triiodoallyl alcohol reactive derivative (III) are added thereto, whereby an iodopropargyl group or a 2,3,3-triiodoallyl group is introduced onto the nitrogen atom in a tetrazole ring. As examples of the inert organic solvent which may be employed in this reaction, there may be mentioned benzene, dioxane, dichloromethane, N,N-dimethylformamide, tetrahydrofuran and the like and N,N-dimethylformamide is preferable. As examples, of the base which may be employed in this reaction, there may be mentioned an organic base such as an alkali hydroxide, an alkali carbonate, an alkali bicarbonate and the like and an organic base such as triethylamine, pyridine and the like. This N-alkylation reaction may proceed rapidly at room temperature, for instance, when an alkali hydroxide is used as the base to effect the reaction with a sulfonic acid ester, but the reaction may be practically carried out under cooling, preferably at −10° C. to 0° C., for prevention of side reactions or the reaction may proceed in the presence of the base even with heating to 40°–60° C.

Of the present compound (I), the iodopropargyltetrazole compound (I-b) may be also prepared according to the following reaction schema B, in addition to the aforesaid reaction schema A.

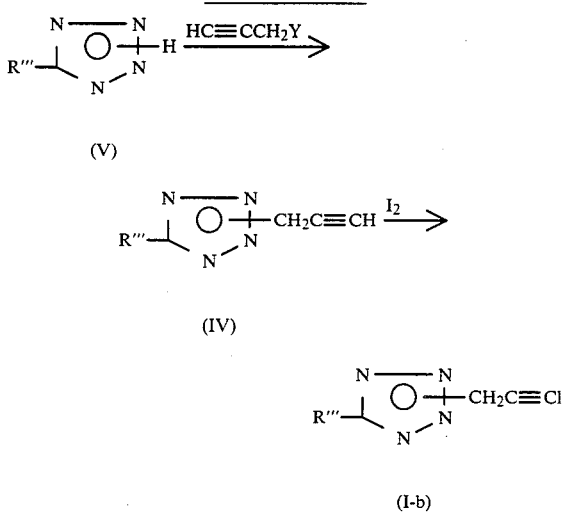

In the above formulae, R''' and Y are as defined above. In this instance, the N-alkylation reaction to react the 5-substituted tetrazole (V) with the propargyl alcohol reactive derivative may be conducted in the same manner as in the aforesaid reaction schema A. The iodination reaction of the 5-propargyl-substituted tetrazole (IV) may be easily conducted by addition of iodine in the presence of a base in an inert organic solvent, thereby yielding the 5-iodopropargyl-substituted tetrazole (I-b). In this step, there may be similarly employed generally the same inert organic solvent and base as used for the N-alkylation step.

After completion of the reaction, the desired tetrazole compound (I) may be easily isolated from the reaction mixture by any conventional method, for example, by precipitation with an inert solvent such as water or extraction with an organic solvent such as benzene, ethyl acetate, dichloromethane or, if necessary, in optional combination with well-known purification methods such as column chromatography over silica gel or recrystallization from an organic solvent.

This invention will be more fully illustrated by way of the following Examples and Preparation Examples. The Examples 1 to 29 illustrate the synthesis of the novel tetrazole compound (I) according to this invention.

EXAMPLE 1

1-(1'-Iodopropyn-3'-yl)-5-methyltetrazole (Compound No. 2) and 2-(1'-iodopropyn-3'-yl)-5-methyltetrazole (Compound No. 1)

To a solution of 420 mg (5 mmoles) of 5-methyltetrazole in 20 ml of dimethylformamide were added 220 mg of powdery sodium hydroxide and the resulting mixture was stirred well under ice-cooling. To the mixture were added 1.50 g (4.5 mmoles) of iodopropargyl alcohol p-toluenesulfonic acid ester and then the reaction was effected under ice-cooling for 5 hours. Thereafter, the reaction mixture was left at 20°–25° C. overnight. To the reaction mixture were added 50 ml of water and the resulting mixture was extracted with 20 ml of ethyl acetate. The ethyl acetate layer washed with water, dried over magnesium sulfate and then concentrated under reduced pressure to give a brown crude product. This crude product was found to be a mixture of two substances having Rf values of 0.61 and 0.21, respectively, by a silica gel thin layer chromatography (solvent system: benzene-ethyl acetate=4:1). The mixture was isolated and purified by a column chromatography using 70 g of silica gel (solvent system: toluene-ethyl acetate=6:1) and 264 mg of 2-(1'-iodopropyn-3'-yl)-5-methyltetrazole as crystals were obtained from fractions of Rf value 0.61 (Yield 23.5%). mp. 112°–113.5° C.

Analysis for $C_5H_5N_4I$ (%): Calc'd: C, 24.21; H, 2.03; N, 22.59; I, 51.17; Found: C, 24.38; H, 2.01; N, 23.06; I, 50.69.

From fractions of Rf value 0.21, there were obtained 457 mg of 1-(1'-iodopropyn-3'-yl)-5-methyltetrazole as crystals (Yield 40.8%) m.p. 90°–93° C.

EXAMPLE 2

2-(1'-Iodopropyn-3'-yl)-5-n-propyltetrazole (Compound No. 5) and 1-(1'-iodopropyn-3'-yl)-5-n-propyltetrazole (Compound No. 6)

A mixture of 1.12 g (10 mmoles) of 5-n-propyltetrazole, 1.24 ml of triethylamine, 3.30 g of iodopropargyl alcohol p-nitrobenzenesulfonic acid ester and 100 ml of benzene was heated under reflux on a water bath for 20 minutes. The reaction mixture was cooled, 50 ml of ethyl acetate were added thereto and the resulting mixture was washed twice with water and then dried over anhydrous sodium sulfate. The organic solvent was distilled off under reduced pressure and a silica gel thin layer chromatography (TLC) (solvent system: benzene-ethyl acetate=10:1) of the so-obtained crude crystal showed to be a mixture of the two substances having Rf values of 0.57 and 0.20, respectively. The crude crystal was recrystallized from a mixed solvent of 10 ml of benzene and 10 ml of hexane to separate prferentially out 707 mg of 1-(1'-iodopropyn-3'-yl)-5-n-propyltetrazole having Rf value of 0.20 (Yield 28%). mp. 95.8°–97.8° C.

Analysis for $C_7H_9N_4I$ (%): Calc'd: C, 30.48; H, 2.83; N, 19.82; Found: C, 30.48; H, 2.83; N, 19.82.

The recrystallization mother liquor was concentrated and the residue was purified by a silica gel column chromatography to afford 441 mg of 2-(1'-iodopropyn-3'-yl)-5-n-propyltetrazole having Rf value 0.57 (Yield 18%). mp. 59.5°–62.0° C.

Analysis for $C_7H_9N_4I$ (%): Found: C, 30.30; H, 2.97; N, 19.87.

EXAMPLE 3

2-(1'-Iodopropyn-3'-yl)-5-isopropyltetrazole (Compound No. 7) and 1-(1'-iodopropyn-3'-yl)-5-isopropyltetrazole (Compound No. 8)

0.56 g (5 mmoles) of 5-isopropyltetrazole and 0.20 g (5 mmoles) of powdery sodium hydroxide were stirred well in anhydrous dimethylformamide to form a homogeneous solution. To this solution were added 1.83 g (5 mmoles) of iodopropargyl alcohol p-nitrobenzenesulfonic acid ester under ice-cooling and the reaction was continued for 2 hours and then at 20°-25° C. for further 2 hours. The reaction mixture was extracted with 100 ml of ethyl acetate and 50 ml of water, the ethyl acetate layer was washed with water, dried over anhydrous sodium sulfate and concentrated under reduced pressure to afford 1.57 g of a crude product. This crude product was further purified by a silica gel column chromatography to give 2-(1'-iodopropyn-3'-yl)-5-isopropyltetrazole and 1-(1'-iodopropyn-3'-yl)-5-isopropyltetrazole, respectively.

The former product was obtained at a yield of 534 mg (39%). m.p. 52.8°-54.3° C.

Analysis for $C_7H_9N_4I$(%): Calc'd: C, 30.45; H, 3.29; N, 20.29; Found: C, 30.03; H, 3.24; N, 20.59.

The latter product was obtained at a yield of 650 mg (47%). m.p. 89.0°-90.8° C.

Analysis for $C_7H_9N_4I$(%): Found: C, 29.77; H, 3.18; N, 20.28.

EXAMPLE 4

2-(1'-Iodopropyn-3'-yl)-5-tert.-butyltetrazole (Compound No. 15) and 1-(1'-iodopropyn-3'-yl)-5-tert.-butyltetrazole (Compound No. 16)

Following the same procedures as in Example 2 except that 504 mg (4 mmoles) of 5-tert.-butyltetrazole and an equal amount of iodopropargyl alcohol p-nitrobenzenesulfonic acid ester were used the reaction was conducted in 15 ml of diemthylformamide under ice-cooling for 2 hours and then at room temperature for further 2 hours, there was prepared a mixture of 2-(1'-iodopropyn-3'-yl)-5-tert.-butyltetrazole and 1-(1'-iodopropyn-3'-yl)-5-tert.-butyltetrazole, from which each product was then isolated and purified by a silica gel chromatography (solvent system: toluene-ethyl acetate=10:1).

The former product, 624 mg (54%), mp. 85.8°-87.7° C.

Analysis for $C_8H_{11}N_4I$ (%): Calc'd: C, 33.12; H, 3.82; N, 19.31; Found: C, 33.17; H, 3.71; N, 19.31.

The latter product, 399 mg (34%), oily substance
Analysis for $C_8H_{11}N_4I$ (%): Found: C, 32.18; H, 3.56; N, 18.33.

EXAMPLE 5

2-(1'-Iodopropyn-3'yl)-5-pentyltetrazole (Compound No. 17) and 1-(1'-iodopropyn-3'-yl)-5-pentyltetrazole (Compound No. 18)

Following the same procedures as in Example 3 except that 0.70 g (5 mmoles) of 5-pentyltetrazole was used and 1.68 g (5 mmoles) of iodopropargyl p-toluenesulfonate were used instead of the p-nitrobenznesulfonate, there was prepared a mixture of 2-(1'-iodopropyn-3'-yl)-5-pentyltetrazole and 1-(1'-iodopropyn-3'-yl)-5-pentyltetrazole, from which each product was isolated by a silica gel chromatography.

The former product, 588 mg (36%), oily substance, mass spectrum (EI) 304 (M+); the latter product, 86.7 mg (57%), oily substance, mass spectrum (EI) 304 (M+).

EXAMPLE 6

2-(1'-Iodopropyn-3'-yl)-5-heptyltetrazole (Compound No. 21) and 1-(1'-iodopropyn-3'-yl)-5-heptyltetrazole (Compound No. 22)

Following the same procedures as in Example 3 except that 0.51 g (3 mmoles) of 5-heptyltetrazole and an equal amount of the same reagent used and the reaction was conducted in 20 ml of dimethylformamide under ice-cooling for 16 hours, there were prepared 1.20 g of a mixture of 2-(1'-iodopropyn-3'-yl)-5-heptyltetrazole and 1-(1'-iodopropyn-3'-yl)-5-heptyltetrazole, from which each product was isolated by a silica gel column chromatography.

The former product, 341 mg (34%), oily substance, mass spectrum (EI) 332 (M+).

The latter product 595 mg (60%), oily substance, mass spectrum (EI) 332 (M+)

EXAMPLE 7

2-(1'-Iodopropyn-3'-yl)-5-ethyltetrazole (Compound No. 3) and 1-(1'-iodopropyn-3'-yl)-5-ethyltetrazole (Compound No. 4)

By using 490 mg (5 mmoles) of 5-ethyltetrazole and equimolar amounts of sodium hydroxide and iodopropargyl p-nitrobenzenesulfonate, the reaction was conducted in 15 ml of diemthylformamide under ice-cooling overnight in the same manner as in Example 3 to produce 1.15 g of the crude mixture (Crude yield 88%). This mixture was subjected to a silica gel column chromatography (solvent system: benzene-ethyl acetate=10:1 to 4:1) to isolate and purify 2-(1'-iodopropyn-3'-yl)-5-ethyltetrazole and 1(1'-iodopropyn-3'-yl)-5-ethyltetrazole.

The former product, 367 mg (28%), mass spectrum (EI) 262 (M+),

Analysis for $C_6H_7N_4I$ (%): Calc'd: C, 27.50; H, 2.69; N, 21.38; Found: C, 26.90; H, 2.60; N, 21.00.

The latter product, 693 mg (53%), mass spectrum (EI) 262 (M+),

Analysis for $C_6H_7N_4I$ (%): Found: C, 27.11; H, 2.73; N, 20.83.

EXAMPLE 8

2-(1'-Iodopropyn-3'-yl)-5-(p-methoxyphenyl)tetrazole (Compound No. 24)

In anhydrous dimethylformamide were stirred well 1.86 g (10 mmoles) of 5-(p-methoxyphenyl)tetrazole and 420 mg (10 mmoles) of sodium hydroxide to form a homogeneous solution. To this solution were added under ice-cooling 3.67 g (10 mmoles) of iodopropargyl p-nitrobenzenesulfonate and the reaction was continued for 4 hours. The reaction mixture was extracted with 200 ml of ethyl acetate and 100 ml of water, the ethyl acetate layer was washed with water, dried and concentrated under reduced pressure. The solid residue, thus obtained was recrystallized twice from methanol to give 2-(1'-iodopropyn-3'-yl)-5-(p-methoxyphenyl)tetrazole, Yield 2.06 g (60%), mp. 146.7°-149.8° C.

Analysis for $C_{11}H_9ON_4I$ (%): Calc'd: C, 38.84; H, 2.67; N, 16.47; Found: C, 37.57; H, 2.58; N, 16.06.

EXAMPLE 9

1-(1'-Iodopropyn-3'-yl)-5-(p-chlorophenyl)tetrazole (Compound No. 26) and 2-(1'-iodopropyn-3'-yl)-5-(p-chlorophenyl)tetrazole (Compound No. 25)

To a solution of 360 mg (2 mmoles) of p-chlorophenyltetrazole in 5 ml of dimethylformamide were added 90 mg of powdery sodium hydroxide and the resulting mixture was stirred and ice-cooled. Then, 0.68 g (2 mmoles) of iodopropargyl p-toluenesulfonate was added thereto and the reaction was conducted under ice-cooling for 4 hours and allowed to stand at 20°-25° C. overnight.

The reaction product was found to be a mixture of two substances having Rf values of 0.86 and 0.61, respectively by a silica gel TLC (solvent system: toluene-ethyl acetate=4:1). The reaction mixture was treated with 20 ml of water, the so-separated crystalline substance was recovered by filtration and recrystallized from methanol to afford 354 mg of the product having Rf value of 0.86 as needles (Yield 51%). mp. 127°-128.5° C.

Analysis for $C_{10}H_6N_4ClI$ (%): Calc'd. C, 34.86; H, 1.76; N, 16.26; Cl, I, 47.12; Found: C, 35.68; H, 1.81; N, 16.42; Cl, I, 45.93.

On the other hand, the mother liquor was subjected to a column chromatography using 20 g of silica gel (solvent system: benzene -ethyl acetate=10:1 to 4:1) to give 116 mg of the product having Rf value of 0.61 (Yield 16.8%). mp. 139.5°-140.5° C.

Analysis for $C_{10}H_6N_4ClI$ (%): Calc'd: C, 34.86 H, 1.76; N, 16.26; Cl, I, 47.12; Found: C, 35.68; H, 1.81; N, 16.42; Cl, I, 45.93.

EXAMPLE 10

2-(1'-Iodopropyl-3'-yl)-5-(m-chlorophenyl)tetrazole (Compound No. 28)

Following the same procedures as in Example 8 except that 3.61 g (20 mmoles) of 5-(m-chlorophenyl)tetrazole and an equimolar amount of iodopropargyl alcohol p-toluenesulfonic acid ester were used and the reaction was conducted in 40 ml of dimethylformamide, there was prepared a crude crystalline substance. This substance was recrystallized from a mixture of methanol and water to give 4.74 g of 2-(1'-iodopropyn-3'-yl)-5-(m-chlorophenyl)tetrazole as pure crystals (Yield 69%). mp. 91.5°-93.2° C.

Analysis for $C_{10}H_6N_4ClI$ (%): Calc'd: C, 34.86; H, 1.76; N, 16.26; Found: C, 34.83; H, 1.70; N, 16.22.

EXAMPLE 11

2-(1'-Iodopropyl-3'-yl)-5-(o-chlorophenyl)tetrazole (Compound No. 27)

Following the same procedures as in Example 8 except that 3.61 g (20 mmoles) of 5-(o-chlorophenyl)tetrazole and an equimolar amount of the same reagent were used and the reaction was conducted in 40 ml of dimethylformamide, there were prepared 5.8 g of the crude oily product. This product was purified by a silica gel chromatography (solvent system: toluene) and then recrystallized from isopropyl ether to give 3.63 g of purified 2-(1'-iodopropyn-3'-yl)-5-(o-chlorophenyl)tetrazole (Yield 44%). mp. 92.5°-93.8° C.

Analysis for $C_{10}H_6N_4ClI$ (%): Calc'd: C, 34.86; H, 1.76; N, 16.26; Found: C, 34.97; H, 1.77; N, 16.46.

EXAMPLE 12

2(1'-Iodopropyn-3'-yl)-5-(m-trifluoromethylphenyl)tetrazole (Compound No. 32)

Following the same procedures as in Example 8 except that 2.14. g (10 mmoles) of 5-(m-trifluoromethylphenyl)tetrazole were used, there were prepared 3.44 g (91%) of the crude reaction product. This crystalline product was recrystallized twice from a mixture of methanol and water to give 2.23 g (59%) of 2-(1'-iodopropyn-3'-yl)-5-(m-trifluoromethylphenyl)tetrazole. mp. 70.0°-72.0° C.

EXAMPLE 13

2-(1'-Iodopropyn-3'-yl)-5-(p-fluorophenyl)tetrazole (Compound No. 29)

Following the same procedures as in Example 8 except that 1.64 g (10 mmoles) of 5-(p-fluorophenyl)tetrazole were employed, there were prepared 2.71 g of the crude product. This product was purified by a silica gel chromatography and then further recrystallized from a mixture of 4 ml of benzene and 46 ml of hexane to give 1.04 g of 2-(1'-iodopropyn-3'-yl)-5-(p-fluorophenyl)tetrazole as pure crystals. mp. 104.6°-106.2° C.

Analysis for $C_{10}H_6N_4IF$ (%): Calc'd: C, 36.61; H, 1.84; N, 17.08; Found: C, 36.67; H, 1.78; N, 17.42.

EXAMPLE 14

2-(1'-Iodopropyn-3'-yl)-5-(p-cyanophenyl)tetrazole (Compound No. 33)

Following the same procedures as in Example 8 except that 1.71 g (10 mmoles) of 5-(p-cyanophenyl)tetrazole were used, there were prepared 3.05 g (95%) of the crude reaction product. This product was recrystallized from 16 ml of acetone to give 1.41 g (42%) of 2-(1'-iodopropyn-3'-yl)-5-(p-cyanophenyl)tetrazole as crystals. mp. 174°-184.6° C.

Analysis for $C_{11}H_6N_5I$ (%): Calc'd: C, 39.43; H, 1.80; N, 20.90; I, 37.87; Found: C, 39.74; H, 1.80; N, 21,16; I, 36.87.

EXAMPLE 15

2-(2'-Iodopropyn-3'-yl)-5-(p-hydroxyphenyl)tetrazole (Compound No. 34) and 1-(1'-iodopropyn-3'-yl)-5-(p-hydroxyphenyl)tetrazole (Compound No. 35)

To a solution of 0.81 g (5 mmoles) of 5-(p-hydroxyphenyl)tetrazole and 200 mg of powdery sodium hydroxide in dimethylformamide were added under ice-cooling 1.84 g (5 mmoles) of iodopropargyl alcohol p-nitrobenzenesulfonic acid ester and the reaction mixture was stirred for 4 hours. The reaction mixture was extracted with 100 ml of ethyl acetate and 50 ml of water, the ethyl acetate layer was washed with water, dried over anhydrous sodium sulfate and concentrated to give 1.23 g (75%) of the crude product. This product was subjected to a column chromatography using 65 g of silica gel (solvent system: hexane-ethyl acetate=1:1) to in turn elute the following two substances; 2-(1'-iodopropyn-3'-yl)-5-(p-hydroxyphenyl)tetrazole, yield 643 mg (39%), mp. 187°-188° C. (recrystallized from isopropyl alcohol) and 1-(1'-iodopropyn-3'-yl)-5-(p-hydroxyphenyl)tetrazole, yield 500 mg, m.p. 179°-180°

C. (recrystallized from isopropyl alcohol).

EXAMPLE 16

2-(1'-Iodopropyn-3'-yl)-5-(p-methylphenyl)tetrazole (Compound No. 31)

To a solution of 173 mg (1.1 mmoles) of 5-p-methylphenyltetrazole in 5 ml of dimethylformamide were added 44 mg of powdery sodium hydroxide and the resulting mixture was stirred well and cooled. To the mixture were added 336 mg (1 mmole) of iodopropargyl alcohol p-toluenesulfonic acid ester and the reaction was conducted at 20°–25° C. for 1 hour and then allowed to stand at 4° C. over two nights. 20 ml of water were added to the reaction mixture, the crystalline substance thus separated was recovered by filtration, washed with water, dried and recrystallized from 3 ml of methanol to give 60.4 mg (16.9%) of 2-(1'-iodopropyn-3'-yl)-5-(p-methylphenyl)tetrazole as dark brown having Rf value of 0.52 on a silica gel TLC (solvent system: benzene). mp. 139.5°–141.0° C.

Analysis for $C_{11}H_9N_4I$ (%): Calc'd: C, 40.76; H, 2.80; N, 17.29; I, 39.15; Found: C, 40.79; H, 2.82; N, 16.70; I, 39.32.

EXAMPLE 17

2-(1'-Iodopropyn-3'-yl)-5-(3'',5''-dichlorophenyl)tetrazole (Compound No. 30)

In 15 ml of dimethylformamide were stirred 645 mg (3 mmoles) of 5-(3',5'-dichlorophenyl)tetrazole and 120 mg of powdery sodium hydroxide to form a homogeneous solution. To this solution were added 357 mg of propargyl bromide and the resulting mixture was allowed to stand at room temperature for 16 hours. The reaction mixture was extracted with 50 ml of the benzene layer was washed with water, dried over anhydrous sodium sulfate and concentrated. The resulting residue (0.78 g) was again dissolved in 100 ml of benzene, 1.02 g (3 mmoles) of morpholine-iodine complex were added thereto and the reaction was conducted with vigorous stirring over 2 days. The reaction mixture was washed with aqueous sodium thiosulfate and water, dried and then concentrated to give 948 mg of the crude iodide product. This product was subjected to a column chromatography using 50 g of silica gel (solvent system: toluene) to give 626 mg of 2-(1'-iodopropyn-3'-yl)-5-(3'',5''-dichlorophenyl)tetrazole as crude crystals, which was then recrystallized from 20 ml of hexane to give 527 mg of the pure crystal (Yield 46%). mp. 102.0°–103.5° C.

Analysis for $C_{10}H_5N_4Cl_2I$ (%): Calc'd: C, 31.69; H, 1.33; N, 14.78; Cl, 18.71; I, 33.48; Found: C, 31.38; H, 1.31; N, 14.91; total halogen, 52.04.

EXAMPLE 18

2-(1'-Iodopropyn-3'-yl)-5-(p-carbamoylphenyl)tetrazole (Compound No. 36)

Following the same procedures as in Example 8 except that 1.89 g (10 mmoles) of 5-(p-carbamoylphenyl)tetrazole and an equimolar amount of the same reagent were employed, there was prepared the crude crystalline substance. This substance was recrystallized twice from acetone to give 1.66 g (60%) of 2-(1'-iodopropyn-3'-yl)-5-(p-carbamoylphenyl)tetrazole as pure crystals. mp. 192.4°–193.7° C.

Analysis for $C_{11}H_8ON_5I$ (%): Calc'd: C, 37.41; H, 2.28; N, 19.83; Found: C, 37.10; H, 2.36; N, 19.56.

EXAMPLE 19

2-(1'-Iodopropyn-3'-yl)-5-(p-nitrophenyl)tetrazole (Compound No. 37)

To a solution of 210 mg (1.1 mmoles) of 5-(p-nitrophenyl)tetrazole in 5 ml of dimethylformamide were added 44 mg of powdery sodium hydroxide and the resulting mixture was stirred well and cooled. 336 mg (1 mmole) of iodopropargyl alcohol p-toluenesulfonic acid ester were added thereto, the reaction was continued at 20°–25° C. over 1 hour and then allowed to stand at 4° C. for two nights. To the reaction mixture were added 20 ml of water, the so-separated crystal was recovered by filtration, washed with 10 ml of water, dried and recrystallized from a total of 20 ml of a small volume of dimethylformamide and methanol to give 74 mg of 2-(1'-iodopropyn-3'-yl)-5-(p-nitrophenyl)tetrazole as pale yellow needles (Yield 19.7%). mp. 188°–190° C.

Analysis for $C_{10}H_6N_4O_2I$ (%): Calc'd: C, 38.90; H, 1.96; N, 18.13; I, 41.10; Found: C, 38.45; H, 1.90; N, 18.01; I, 39.95.

EXAMPLE 20

2-(1'-Iodopropyn-3'-yl)-5-(p-carboxyphenyl)tetrazole (Compound No. 38)

Following the same procedures as in Example 8 except that 0.92 g (5 mmoles) of 5-(p-carboxyphenyl)tetrazole and an equimolar amount of the same reagent were used and the reaction was conducted in 5 ml of dimethylformamide, there were prepared 1.15 g (65%) of the crude crystalline product. This product was subjected to a silica gel column chromatography (solvent system: ethyl acetate) to isolate only the substance having Rf value of 0.66 by a silica gel TLC using ethyl acetate, i.e. pure 2-(1'-iodopropyn-3'-yl)-5-(p-carboxyphenyl)tetrazole, 438 mg (25%). This substance was recrystallized from 10 ml of methanol to give 269 mg of a pure crystal. mp. 210.8°–211.5° C.

EXAMPLE 21

2-(1'-Iodopropyn-3'-yl)-5-(p-dimethylaminophenyl)tetrazole (Compound No. 39)

To a solution of 420 mg (2.2 mmoles) of 5-(p-dimethylaminophenyl)-tetrazole and 84 mg of powdery sodium hydroxide in 5 ml of dimethylformamide were added under ice-cooling 672 mg (2 mmoles) of iodopropargyl alcohol p-toluenesulfonic acid ester. The reaction mixture was gradually raised to room temperature over 5 hours. To the reaction mixture were added 20 ml of ice-water to separate out of viscous substance. After removing supernatant, 5 ml of methanol were added to separate out 2-(1'-iodopropyn-3'-yl)-5-(p-dimethylaminophenyl)tetrazole as crystals.

Yield 300 mg (43%). mp. 164.5°–166° C.

Analysis for $C_{12}H_{12}N_5I$ (%): Calc'd: C, 40.81; H, 3.43; N, 19.83; Found: C, 40.18; H, 3.24; N, 19.03.

EXAMPLE 22

2-(1'-Iodopropyn-3'-yl)-5-phenyltetrazole (Compound No. 23)

To a solution of 4.38 g (30 mmoles) of 5-phenyltetrazole in 50 ml of dimethylformamide were added 5.01 ml (36 mmoles) of triethylamine and 2.56 ml (33 mmoles) of propargyl bromide and the reaction was conducted at 20°–25° C. for 3 hours. To the reaction mixture were added 200 ml of ice-water and the resulting mixture was extracted with 300 ml of the solvent system, ethyl acetate—hexane=1:1. The solvent layer was washed three times with each 30 ml portion of water, dried over anhydrous sodium sulfate and concentrated under reduced pressure to give a crude product. This product was treated with 20 ml of benzene and the benzene layer was concentrated to give crude 2-(propyn-3′-yl)-5-phenyltetrazole as a pale yellow oily substance (Yield 3.0 g, 57%).

To a solution of 175 mg (1 mmole) of the above oily substance in 5 ml of benzene were added 332 mg (1 mmole) of morpholine-iodine complex and stirring was done at 20°–25° C. overnight. The reaction mixture was filtered and the filtrate was extracted with 50 ml of benzene and 50 ml of water. The benzene layer was discolored with aqueous sodium thiosulfate, dried over anhydrous magnesium sulfate, and concentrated under reduced pressure to give a pale yellow crude product. This product was subjected to a column chromatography using 20 g of silica gel (solvent system: benzene) to isolate the substance having Rf value of 0.73 on a silica gel TLC (solvent system: benzene—ethyl acetate=10:1), which was then recrystallized from 1.5 ml of methanol to give 71.3 mg of colorless needles (23%). mp. 126°–128.5° C.

EXAMPLE 23

2-(2′,3′,3′-Triiodoallyl)-5-n-heptyltetrazole (Compound No. 40) and 1-(2′,3′,3′-triiodoallyl)-5-n-heptyltetrazole (Compound No. 41)

To a solution of 6.83 g of 5-n-heptyltetrazole in 100 ml of dry benzene were added 23.8 g of 2,3,3-triiodoallyl-p-nitrobenzenesulfonate and 4 g of triethylamine and the reaction was effected for 1.5 hours. The reaction mixture was washed with aqueous sodium hydrogencarbonate and dried over anhydrous magnesium sulfate. The benzene solution was concentrated under reduced pressure to give a mixture of 2-(2′,3′,3′-triiodoallyl)-5-n-heptyltetrazole and 1-(2′,3′,3′-triiodoallyl)-5-n-heptyltetrazole. A crude yield 22.4 g (48%). Two grams of this crude mixture were subjected to a column chromatography using 40 g of silica gel (solvent system: toluene—ethyl acetate=10:1 to 4:1) to isolate the substances, respectively.

The former product, yield 1.19 g, colorless needles, mp. 69.8°–70.2° C. (recrystallized from water-methanol).

Analysis for $C_{11}H_{17}N_4I_3$ (%): Calc'd: C, 22.55; H, 2.92; N, 9.56; I, 64.97; Found: C, 22.46; H, 2.85; N, 9.32.

The latter product, yield 0.68 g, brown solid.

Analysis for $C_{11}H_{17}N_4I_3$ (%): Calc'd: C, 22.55; H, 2.92; N, 9.56; I, 64.97; Found: C, 23.10; H, 2.81; N, 9.44; I, 63.16.

EXAMPLE 24

2-(2′,3′,3′-Triiodoallyl)-5-n-pentyltetrazole (Compound No. 42) and 1-(2′,3′,3′-triiodoallyl)-5-n-pentyltetrazole (Compound No. 43)

To a solution of 0.70 g of 5-n-pentyltetrazole in 10 ml of dimethylformamide was added 0.20 g of powdery sodium hydroxide to form a homogeneous solution. To this solution were added under ice-cooling 2.94 g of 2,3,3-triiodoallyl p-toluenesulfonate and the reaction was conducted under cooling for 1 hour and then at room temperature overnight. The reaction mixture was extracted with 100 ml of ethyl acetate and 50 ml of water. The ethyl acetate layer was washed with a saturated aqueous solution of sodium chloride, dried and then concentrated to leave a pale red solid material. Yield 2.63 g (95%). This crude product was purified by a silica gel chromatography (solvent system: benzene—ethyl acetate=10:1 to 4:1) to separate 2-(2′,3′,3′-triiodoallyl)-5-n-pentyltetrazole and 1-(2′,3′,3′-triiodoallyl)-5-n-pentyltetrazole.

The former product, 0.83 g. (29%), pale red oily substance.

Analysis for $C_9H_{13}N_4I_3$ (%): Calc'd: C, 19.37; H, 2.35; N, 10.04; Found: C, 19.00; H, 2.27; N, 9.95.

The latter product, 1.45 g (52%), mp. 105.4°–107.3° C.

Analysis for $C_9H_{13}N_4I_3$ (%): Calc'd: C, 19.37; H, 2.35; N, 10.04; Found: C, 19.50; H, 2.32; N, 9.82.

EXAMPLED 25

2-(2′,3′,3′-Triiodoallyl)-5-tert.-butyltetrazole (Compound No. 44) and 1-(2′,3′,3′-triiodoallyl)-5-tert.-butyltetrazole (Compound No. 45)

A mixture of 252 mg of 5-tert.-butyltetrazole, 1.40 g of 2,3,3-triiodoallyl-p-nitrobenzenesulfonate and 15 ml of benzene was heated under reflux on a water bath for 30 minutes. The reaction mixture was cooled, washed twice with water, dried over anhydrous sodium sulfate and concentrated to give a mixture of 2-(2′,3′,3′-triiodoallyl)-5-tert.-butyltetrazole and 1-(2′,3′,3′-triiodoallyl)-5-tert.-butyltetrazole as a solid. This solid was recrystallized from 2 ml of methanol to give the former product as colorless crystals. Yield 568 mg (52%), mp. 108°–110° C.

Analysis for $C_8H_{11}N_4I_3$ (%): Calc'd: C, 17.67; H, 2.04; N, 10.38; Found: C, 17.70; H, 1.89; N, 9.61.

The methanol mother liquor was concentrated and the residue was purified by a silica gel chromatography to give further 0.41 g of the former and 0.20 g of the latter.

EXAMPLE 26

2-(2′,3′,3′-Triiodoallyl)-5-n-propyltetrazole (Compound No. 46) and 1-(2′,3′,3′-triiodoallyl)-5-n-propyltetrazole (Compound No. 47)

Following the same procedures as in Example 24 except that 426 mg (3.8 mmoles) of 5-n-propyltetrazole and an equal amount of 2,3,3-triiodoallyl p-nitrobenzenesulfonate were used and the reaction was conducted in benzene at 60° C. for 30 minutes, there were prepared 2.03 g (99%) of a mixture of 2-(2′,3′,3′-triiodoallyl)-5-n-propyltetrazole and 1-(2′,3′,3′-triiodoallyl)-5-n-propyltetrazole. This mixture was subjected to a silica gel chromatography (solvent system: toluene—ethyl acetate=10:1 to 4:1) to separate the respective products.

The former product, 609 mg (30%), mp. 85.3°–87.2° C.

Analysis for $C_7H_9N_4I_3$ (%): Calc'd: C, 15.87; H, 1.71; N, 10.57; Found: C, 15.91; H, 1.64; N, 10.30.

The latter product, 1.27 g (63%), mp. 130.1°–132.5° C.

Analysis for $C_7H_9N_4I_3$ (%): Calc'd: C, 15.87; H, 1.71; N, 10.57; Found: C, 15.84; H, 1.61; N, 10.38.

EXAMPLE 27

2-(2',3',3'-Triiodoallyl)-5-isopropyltetrazole (Compound No. 48) and 1-(2',3',3'-triiodoallyl)-5-isopropyltetrazole (Compound No. 49)

Following the same procedure as in Example 24 except that 560 mg (5 mmoles) of 5-isopropyltetrazole and an equal amount of 2,3,3-triiodoallyl p-nitrobenzenesulfonate were used and the reaction was conducted in benzene at 60° C. for 35 minutes, there were prepared 2.62 g (98%) of a mixture of 2-(2',3',3'-triiodoallyl)-5-isopropyltetrazole and 1-(2',3',3'-triiodoallyl)-5-isoprolyltetrazole. This mixture was subjected to a column chromatography using 100 g of silica gel (solvent system; toluene-ethyl acetate=10:1) to isolate the respective products.

The former product, 1.00 g (36%), mp. 113.0°–114.7° C.

Analysis for $C_7H_9N_4I_3$ (%): Calc'd: C, 15.87; H, 1.71; N, 10.57; Found: C, 15.64; H, 1.60; N, 10.41.

The latter product, 1.33 g (50%), mp. 173.0°–176.5° C.

Analysis for $C_7H_9N_4I_3$ (%): Calc'd: C, 15.87; H, 1.71; N, 10.57; Found: C, 15.65; H, 1.62; N, 10.40.

EXAMPLE 28

2-(2',3',3'-Triiodoallyl)-5-benzyltetrazole (Compound No. 58) and 1-(2',3',3'-triiodoallyl)-5-benzyltetrazole (Compound No. 59)

Following the same procedures as in Example 24 except that 320 mg (2 mmoles) of 5-benzyltetrazole and an equal amount of 2,3,3-triiodoallyl p-nitrobenzenesulfonate were used and the reaction was conducted in benzene at 60° C. for 1 hour, there were prepared 1.23 g (97%) of a mixture of 2-(2',3',3'-triiodoallyl)-5-benzyltetrazole and 1-(2',3',3'-triiodoallyl)-5-benzyltetrazole. This mixture was subjected to a silica gel chromatography to separate the respective products.

The former product, 405 mg (35%), mp. 141.7°–146.9° C.

Analysis for $C_{11}H_9N_4I_3$ (%): Calc'd: C, 22.86; H, 1.57; N, 9.70; Found: C, 23.37; H, 1.54; N, 9.79.

The latter product, 601 mg (52%), mp. 142.0°–143.2° C.

Analysis for $C_{11}H_9N_4I_3$ (%): Calc'd: C, 22.86; H, 1.57; N, 9.70; Found: C, 22.98; H, 1.50; N, 9.50.

EXAMPLE 29

2-(2',3',3'-iiodoallyl)-5-ethyltetrazole (Compound No. 50) and 1-(2',3',3'-triiodoallyl)-5-ethyltetrazole (Compound No. 51)

Following the same procedures as in Example 24 except that 485 mg (5 mmoles) of 5-ethyltetrazole and an equivalent amount of 2,3,3-triiodoallyl p-nitrobenzenesulfonate were used and the reaction was conducted in 30 ml of benzene at 60° C. for 1 hour, there was prepared a mixture of 2-(2',3',3'-triiodoallyl)-5-ethyltetrazole and 1-(2',3',3'-triiodoallyl)-5-ethyltetrazole. This mixture was subjected to a silica gel chromatography (solvent system: benzene—ethyl acetate=10:1 to 4:1) to separate the respective products.

The former product, 0.72 g (28%).

Analysis for $C_6H_7N_4I_3$ (%): Calc'd: C, 13.97; H, 1.37; N, 10.86; Found: C, 14.22; H, 1.41; N, 10.55.

The latter product, 1.63 g (62%).

Analysis for $C_6H_7N_4I_3$ (%): Calc'd: C, 13.97; H, 1.37; N, 10.86; Found: C, 13.99; H, 1.47; N, 9.99.

The novel tetrazole compound (I) of this invention is useful as antifungal agents. In particular, the present compound can exert a growth inhibition activity against a wide variety of fungi and thus useful for improvement in undesired conditions caused by growth of bacteria and fungi in all medical, agricultural and industrial fields. More specifically, the present compound can be utilized for medical purposes, for instance, as therapeutic agents against external diseases caused by fungi, typically those belonging to the genera of Candida, Aspergillus, Trichophyton, Cryptococcus and the like, may be formulated as an active ingredient for solutions and ointments in the range of 0.1–5%, preferably 0.5–2%, and accomplish therapeutic purposes by applying to diseased parts. Moreover, the present compound may be utilized as an active ingredient for disinfectants of machines and instruments and others for the purposes of preventing growth of pathogenic bacteria and fungi and maintaining aseptic environment as medicinal use. And further, the present compound may be used as bactericidal, fungicidal and disinfectant agents for prevention of growth of pathogenic bacteria and fungi or treatmennt of external diseases caused thereby for other medicinal uses or veterinary uses for animals such as pet animals, domestic animals and so on. In addition, the present compound may be useful in agricultural and industrial fields. Especially, it is said in these fields that a serious damage would be caused to values of products by development of saprogenous bacilli and fungi in agricultural and industrial products such as seeds, seedlings, woods, wooden products, paper industrial art products, leathers, fibers, adhesives, paints, pulps, cooling water, synthetic resins and the like, as well as their manufacture environment. The present compound can show a growth inhibiting activity against harmful bacteria and fungi in such agricultural and industrial fields and, accordingly, may be provided for preserving quality of products and environment in these fields.

In agricultural and industrial fields, the present compound may be usually applied in the form of a preparation containing the said compound with a conventional carrier; typically, there may be mentioned oil-soluble liquids, emulsions, pastes, dusts, wettable powders, aerosols, antifungal paints, adhesives and so on. As the carrier which may be employed in this invention, there may be mentioned, for example, inorganic solid carriers such as clay, talc, bentonite, kaolin, silicic anhydride, calcium carbonate and the like; organic solvent-type carriers such as kerosine, ligroin, xylene, dimethylformamide, dimethyl sulfoxide and the like; and gaseous carriers such as dimethyl ether, fureon gas and the like. As the auxiliary agent which may be employed for enhancing activities of the present preparation, there may be mentioned, for example, ionic or non-ionic surface active agents, polymeric compounds such as vinyl acetate, methyl cellulose and the like. Also, there may be employed other antifungals or preservatives such as thiabendazole and the like or organic phosphorus insecticides or fungicides, in combination with the present compound.

In preparations containing the present compound, a content of said active ingredient may vary depending upon the form of a preparation, but it is usually suitable to contain the active ingredient in the range of 0.01–95% by weight, preferably 0.2–10% by weight.

Usefulness of the present compound will be more fully illustrated by way of the following activity data against various bacteria and fungi.

TABLE 1

| | Antibacterial Activity (Paper-disc method) | | | |
|---|---|---|---|---|
| | Inhibition zone diameter (mm) | | | |
| | Compound No. 25 | | Compound No. 31 | |
| Test Organism | 500 (γ/ml) | 250 (γ/ml) | 500 (γ/ml) | 250 (γ/ml) |
| Staphylococcus aureus 209P | 13.7 | 13.2 | 11.4 | 11.3 |
| Bacillus subtilis | 11.1 | 11.2 | 9.6 | 9.6 |
| Sarcina lutea | 15 | 16 | 12 | 12 |
| Escherichia coli NIHJ JC-2 | 13.0 | 13.0 | 11.6 | 11.4 |

TABLE 2

| | (Minimal Inhibitory Concentration Method) | | | | |
|---|---|---|---|---|---|
| | Minimal Inhibitory Conc. (mcg/ml) | | | | |
| Test Organism | Compound No. 5 | Compound No. 7 | Compound No. 45 | Compound No. 48 | Compound No. 59 |
| Staphylococcus aureus 209P JC-1 | 12.5 | 12.5 | 0.78 | 1.56 | 1.56 |
| Staphylococcus epidermidis ATCC 14990 | | | 0.20 | 0.39 | 0.20 |
| Bacillus anthracis No. 119 | 12.5 | 12.5 | | | |
| Bacillus subtilis ATCC 6633 | | | 0.78 | 0.39 | 1.56 |
| Escherichia coli NIHJ JC-2 | 50 | 25 | | | |
| Escherichia coli No. 29 | | | 6.25 | 6.25 | 0.78 |
| Salmonella typhi 0-901-W | 25 | 25 | 50 | 12.5 | 12.5 |
| Shigella sonnei EW 33 type I | 6.25 | 6.25 | | | |
| Shigella dysenteriae | | | 3.13 | 3.13 | 0.39 |
| Klebsiella pneumoniae PCI 602 | 100 | 100 | | | |
| Proteus vulgaris OX-19 | 12.5 | 12.5 | 3.13 | 6.25 | 1.56 |
| Serratia marcescens MB-3848 | 25 | 25 | 12.5 | 12.5 | 3.13 |
| Pseudomonas cepacia M-0527 | 100 | >100 | 12.5 | 6.25 | 3.13 |
| Pseudomonas maltiophilia M-0627 | 25 | 50 | | | |

TABLE 3

| | B. Antifungal Activity | | | | |
|---|---|---|---|---|---|
| | Minimal Inhibitory Concentration (MIC) (γ/ml) (in medicinal field) | | | | |
| | Test organism | | | | |
| Test compound No. | Candida albicans GA-24 | Cryptococcus neoformans Cr-1 | Trichophyton metagrophytes 530324 | Trichophyton interdigitale | Aspergillus fumigatus Saito |
| 1 | 6.25 | 3.12 | 3.12 | 6.25 | 6.25 |
| 2 | 1.56 | 0.78 | 0.78 | 0.78 | 0.75 |
| 5 | 0.78 | 0.78 | 0.05 | ≦0.05 | ≦0.05 |
| 7 | ≦0.05 | 0.78 | ≦0.05 | ≦0.05 | ≦0.05 |
| 17 | 3.13 | 3.13 | ≦0.05 | 0.09 | 0.39 |
| 24 | 12.5 | 50 | ≦0.05 | 0.09 | 1.56 |
| 25 | 1.56 | 0.78 | 0.09 | 0.39 | 0.39 |
| 26 | 0.78 | 0.78 | <0.04 | 0.19 | 0.78 |
| 30 | 0.78 | 0.78 | 0.09 | ≦0.05 | 0.19 |
| 31 | 0.78 | 1.56 | 0.19 | 0.39 | 1.56 |
| 35 | 1.56 | 0.39 | 0.10 | 0.10 | 100 |
| 37 | 25 | 3.13 | <0.04 | 0.39 | 6.25 |
| 40 | 6.25 | 6.25 | 0.78 | 0.78 | 6.25 |
| 41 | >100 | 100 | 0.78 | ≦0.05 | 3.13 |
| 42 | 3.13 | 0.78 | 0.09 | 0.19 | 0.78 |
| 43 | 12.5 | 50 | 0.09 | ≦0.05 | 0.39 |

TABLE 3-continued

B. Antifungal Activity
Minimal Inhibitory Concentration (MIC) (γ/ml) (in medicinal field)

| Test compound No. | Candida albicans GA-24 | Cryptococcus neoformans Cr-1 | Trichophyton metagrophytes 530324 | Trichophyton interdigitale | Aspergillus fumigatus Saito |
|---|---|---|---|---|---|
| 44 | 50 | 50 | 0.39 | 0.39 | 6.25 |
| 46 | 1.56 | 0.78 | ≦0.05 | 0.09 | 0.39 |
| 47 | 6.25 | 6.25 | ≦0.05 | 0.09 | 0.78 |
| 48 | 12.5 | 12.5 | 0.78 | 0.78 | 3.13 |
| 49 | 12.5 | 6.25 | 6.25 | 1.56 | 12.5 |

TABLE 4

Antifungal Activity (in Industrial Field)

| Test compound No. | Aspergillus niger ATCC 6275 | Aspergillus flavus ATCC 9643 | Aspergillus terreus PQVD 82j | Penicillium citrinum ATCC 9849 | Penicillium funiculosum ATCC 9644 | Rhizopus stolonifer K203 | Penicillium luteum ATCC 9644 | Mucor spinescens IAM Mu3 |
|---|---|---|---|---|---|---|---|---|
| 5 | 0.78 | 0.78 | 0.20 | 1.56 | 0.78 | 3.13 | | 0.78 |
| 7 | 0.39 | 0.78 | 0.39 | 3.13 | 0.78 | 3.13 | | 0.78 |
| 17 | 0.39 | 0.78 | 0.20 | 1.56 | 0.78 | 12.5 | | 0.39 |
| 26 | 1.56 | 3.13 | 3.13 | 3.13 | 0.78 | +++ | | 1.56 |
| 27 | 25 | 12.5 | 0.78 | 1.56 | 3.13 | 12.5 | | 3.13 |
| 29 | 1.56 | 0.39 | 0.39 | 0.78 | 0.39 | 3.13 | | 0.39 |
| 32 | 1.56 | 1.56 | 1.56 | 1.56 | 1.50 | 6.25 | | 0.39 |
| 46 | 3.13 | 6.25 | 1.56 | | | | 1.56 | 6.25 |
| 58 | 0.78 | 0.78 | 0.39 | | | | 0.78 | 0.78 |

| Test compound No. | Cladsporium herbarum IAM F517 | Pullularia pullulans IAM F24 | Gliocladium virens USDAT-1 ATCC 9645 | Chaetomium globosum ATCC 8059 | Chaetomium globosum ATCC 6205 | Aspergillus fumigatus IAM 3006 | Aspergillus fumigatus IAM 2621 |
|---|---|---|---|---|---|---|---|
| 5 | 1.56 | 1.56 | 1.56 | 50 | | 0.78 | |
| 7 | 3.13 | 6.25 | 3.13 | 12.5 | | 0.78 | |
| 17 | 3.13 | 1.56 | 3.13 | 50 | | 6.25 | |
| 26 | 6.25 | 3.13 | 6.25 | 6.25 | | 30 | |
| 27 | 6.25 | 1.56 | 6.25 | 50 | | 25 | |
| 29 | 1.56 | 3.13 | 3.13 | 6.25 | | 0.78 | |
| 32 | 3.13 | 3.13 | 6.25 | 6.25 | | 50 | |
| 46 | 25 | 3.13 | | | 50 | | 3.13 |
| 58 | 3.13 | 1.56 | | | 6.25 | | 0.39 |

Preparation example of agricultural and industrial antifungal compositions according to this invention are given below. In the following examples, all parts are given by weight unless otherwise stated.

I. WETTABLE POWDERS

Preparation Example 1

Forty parts of 2-(1'-iodopropyn-3'-yl)-5-propyltetrazole, 5 parts of polyoxyethylene alkyl aryl ether, 3 parts of lignin sulfonic acid and 52 parts of diatomaceous earth were uniformly pulverized and admixed to give a wettable powder containing 40% of the active ingredient.

Preparation Example 2

Forty parts of 1-(1'-iodopropyn-3'-yl)-5-methyltetrazole, 5 parts of polyoxyethylene alkyl aryl ether, 3 parts of lignin sulfonic acid and 52 parts of diatomaceous earth were uniformly pulverized and admixed to give a wettable powder containing 40% of the active ingredient.

II. GRANULES

Preparation Example 3

Twelve parts of 2-(1'-iodopropyn-3'-yl)-5-propyltetrazole, 1 part of calcium lignin sulfonate, 30 parts of bentonite and 57 parts of clay were uniformly pulverized and admixed and the resulting mixture was kneaded with a suitable volume of water, granulated and dried to give a granule containing 12% of the active ingredient.

Preparation Example 4

Twelve parts of 2-(1'-iodopropyn-3'-yl)-5-methyltetrazole, 1 part of calcium lignin sulfonate, 30 parts of bentonite and 57 parts of clay were uniformly pulverized and admixed and the resulting mixture was kneaded with a suitable volume of water, granulated and dried to give a granule containing 12% of the active ingredient.

III. EMULSIFIABLE CONCENTRATES

Preparation Example 5

Twenty parts of 2-(1'-iodopropyn-3'-yl)-5-isopropyltetrazole, 30 parts of dimethylformamide, 35 parts of xylene and 15 parts of polyoxyethylene alkyl aryl ether were uniformly admixed to give an emulsifiable concentrate containing 20% of the active ingredient.

Preparation Example 6

Twenty parts of 2-(1'-iodopropyn-3'-yl)-5-methyltetrazole, 30 parts of dimethylformamide, 35 parts of xylene and 15 parts of polyoxyethylene alkyl aryl ether were uniformly admixed to give an emulsifiable concentrate containing 20% of the active ingredient.

IV. DUSTS

Preparation Example 7

Three parts of 2-(1'-iodopropyn-3'-yl)-5-isopropyltetrazole, 0.5 part of silicic acid anhydride fine powder, 0.5 part of calcium stearate, 50 parts of clay and 46 parts of talc were uniformly pulverized and admixed to give a dust containing 3% of the active ingredient.

Preparation Example 8

Three parts of 2-(1'-iodopropyn-3'-yl)-5-methyltetrazole, 0.5 part of silicic acid anhydride fine powder, 0.5 part of calcium stearate, 50 parts of clay and 46 parts of talc were uniformly pulverized and admixed to give a dust containing 3% of the active ingredient.

What is claimed is:

1. A tetrazole compound having the formula

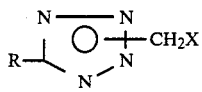

wherein

X represents a group of —C≡CI or a group of —CI=CI$_2$ and R represents an alkyl group having 2–7 carbon atoms, a phenyl group, a methoxyphenyl group, a mono- or di-halogenophenyl group, a trifluoromethyl group, a cyanophenyl group, a hydroxyphenyl group, a carbamoylphenyl group, a carboxyphenyl group, a dimethylaminophenyl group, a nitrophenyl group, a methylphenyl group or a benzyl group.

2. A compound according to claim 1 wherein X is a group of —CI=CI$_2$ and R is an alkyl group having 2–7 carbon atoms or a benzyl group.

3. An antibacterial and antifungal composition which comprises as an active ingredient a tetrazole compound having the formula

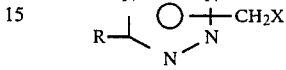

wherein

X represents a group of —C≡CI or a group of —CI=CI$_2$, and R represents an alkyl group having 2–7 carbon atoms, a phenyl group, a monohalogenophenyl group, a methoxyphenyl group, a methylphenyl group, a hydroxyphenyl group or a nitrophenyl group.

4. An antibacterial and antifungal composition according to claim 3 wherein X is a group of —CI=CI$_2$ and R is an alkyl group having 2–6 carbon atoms or a benzyl group.

* * * * *